United States Patent [19]

Ruyak et al.

[11] Patent Number: 4,466,276

[45] Date of Patent: Aug. 21, 1984

[54] CONSISTOMETER

[75] Inventors: Robert F. Ruyak; Stephen G. Ratkowski; Samuel D. Ciprich; Theodore R. Silver, all of Erie, Pa.

[73] Assignee: Autoclave Engineers, Inc., Erie, Pa.

[21] Appl. No.: 425,871

[22] Filed: Sep. 28, 1982

[51] Int. Cl.³ .......................................... G01N 11/00
[52] U.S. Cl. .......................................... 73/59; 73/54
[58] Field of Search ..................................... 73/59, 54

[56] References Cited

U.S. PATENT DOCUMENTS 3,073,151  1/1963  Fann ........................................ 73/54
3,181,348  5/1965  Lewis ...................................... 73/54
3,239,325  3/1966  Roberson et al. ................... 73/59 X

OTHER PUBLICATIONS

API Specification for Materials and Testing for Well Cements of the American Petroleum Institute, (Jan. 1982), pp. 22, 23, 26, 27, and 28.

Primary Examiner—Gerald Goldberg
Assistant Examiner—Vincent P. Kovalick
Attorney, Agent, or Firm—Webb, Burden, Robinson & Webb

[57] ABSTRACT

A high temperature and high pressure consistometer comprises a cylindrical pressure vessel having an integral bottom and a cover for said pressure vessel. A nonmagnetic canister extends downwardly from said bottom and is sealed therein. A driven magnet assembly is journaled in said canister. A drive shaft is connected to said driven magnet assembly extending into said vessel. A nonmagnetic canister extends upwardly from the cover and is sealed therein. A driving magnet assembly is journaled in said canister. A shaft connected to said driving magnet assembly extends downwardly into said vessel. A driven magnet assembly is mounted for rotation on the exterior of the downwardly extending canister and a driven magnet assembly is mounted for rotation on the exterior of the upwardly extending canister. A sample cup is connected to the upwardly extending drive shaft and a paddle is connected to the downwardly extending shaft. External the vessel is positioned an instrument for measuring the torque magnetically transferred from the shaft carrying the paddle to the driven magnet assembly. External the vessel is a motor for causing the driving magnet assembly to rotate at a constant speed to thereby drive the cup within the vessel at a constant speed.

11 Claims, 2 Drawing Figures

CONSISTOMETER

DESCRIPTION

BACKGROUND

Drilling oil and geothermal wells requires the use of drilling muds and well cements. These materials are especially designed for their properties at elevated temperatures and pressures. For development and testing of drilling muds and well cements, pressure vessels are required to simulate the down hole conditions. Pressurized consistometers for measuring thickening times and other properties already exist. With them, samples are tested in a rotating slurry cup with a stationary internal paddle. The consistency of the sample is measured as a function of the time under carefully controlled conditions of increasing temperature and pressure. In fact, standardized equipment and procedures are described in the *Specification for Materials and Testing for Well Cements* issued by The American Petroleum Institute (January 1982). Typically pressurized consistometers have been designed for a working pressure of 25,000 psi at a maximum temperature of 400° F. The consistometer has consisted of a cup (for holding the well cement to be tested), a drive for rotating the cup at a constant speed (usually 150 rpm), and a paddle extending into the container which paddle is associated with a torque measuring transducer. Typically, the drive for rotating the container (or slurry cup as it is often called) passes through the vessel bottom through a high pressure packing. The torque measuring transducer has been positioned within the vessel in the form of a rotation detecting potentiometer and a standardized torsion spring. Electrical leads from the potentiometer pass through the top sides of the vessel. The vessel interior has been heated by electrical heating elements and pressurized by a hydraulic system (the specimen cup has a diaphragm over the top which substantially separates the pressurizing oil from the cement specimen being tested). Recently, packings through which the cup is driven have been replaced by permanent magnet drives.

Because deeper and deeper bores are being drilled and because of the increasing activity in the area of geothermal wells which bores are hotter, higher pressures (say 40,000 psi) and higher temperatures (say, 750° F.) are being encountered. Thus better equipment for testing materials (muds and cements) at higher temperatures and pressures is required. The thermal performances is not simply a matter of maximum temperature but also a heating rate. Thus, increased heating rates in the range of 10° F. per minute are sought.

SUMMARY OF THE INVENTION

It is an object of this invention to provide a higher temperature, higher pressure consistometer.

It is another object of this invention to provide a packless consistometer in which the torque measuring instrumentation is external to the pressure vessel. It is yet another object of this invention to provide a pressurized consistometer having a rapid temperature rise capability.

It is yet another object of this invention to provide a pressurized consistometer that is sealed by only three O-rings that are easily replaceable.

Briefly, according to this invention, there is provided a high temperature and high pressure consistometer comprising a cylindrical pressure vessel having an integral bottom and a cover for said pressure vessel. Apparatus are provided for securing and sealing the cover to the vessel. Preferably, the pressure vessel includes a pressure wall having a cylindrical inner surface and a cylindrical liner having a generally cylindrical outer surface for abutting the inner surface of the pressure wall. The liner has a plurality of grooves therein defining a pathway for circulating cooling fluid. Openings in the pressure wall communicate with the grooves in the liner. The pressure wall is thicker near the bottom of the vessel forming a seat for restricting the downward movement of the vessel liner. Preferably, the cover comprises a nonrotating plug having a collar at the lower end thereof. The apparatus for securing the cover to the vessel comprises a gland sleeve slidably positioned on the plug. The gland sleeve has an axial end face for abutting the collar on the plug. The gland sleeve also has external threads for engaging internal threads in the vessel. Preferably the cover carries an O-ring that abuts a smooth inner cylindrical surface of the liner.

A nonmagnetic canister extends downwardly from the bottom of the vessel and is sealed therein. A driven magnet assembly is journaled in said canister. A drive shaft connected to said driven magnet assembly extends up into the vessel. Preferably the liner has a countersunk well at the lower end. The downwardly extending nonmagnetic canister has a collar at the upper end thereof for seating in and abutting the countersunk well at the lower end of the liner. There is an annular groove between the surface of the well in the liner and the collar on the nonmagnetic canister for capturing an O-ring seal.

A nonmagnetic canister extends upwardly from the cover and is sealed therein. A driving magnet assembly is journaled in said canister. A shaft connected to said driving magnet assembly extends downwardly into the vessel. The plug of the cover preferably has an axial bore with a countersunk well therein at its lower end. The upwardly extending nonmagnetic canister has a collar at the lower end thereof for seating in and abutting the countersunk well in the plug. There is an annular groove between the surface of the well and the plug and the collar on the nonmagnetic canister for capturing an O-ring seal.

A first driving magnet assembly is mounted for rotation on the downwardly extending canister and a driven magnet assembly is mounted for rotation on the upwardly extending canister. A sample cup is connected to the upwardly extending drive shaft and a paddle connected to the downwardly extending driven shaft is positioned within the cup.

Electrical resistance heating elements are spaced about the inside of the cylindrical wall of the vessel. Ports are provided in the bottom of the vessel for introducing pressurized fluids. External the pressure vessel an apparatus for measuring torque magnetically transferred to the driven magnet assembly is mounted relative to the cover. A motor is provided for driving the driving magnet assembly to rotate at a constant speed to thereby drive the cup within the vessel at a constant speed.

Preferably a heat shield consisting of a first group of spaced reflective sheets surrounds the inner side wall of the vessel outside of the heating elements and a second group of spaced reflective sheets beneath the vessel cover. The spaces between the sheets are open communication with the interior of the vessel.

THE DRAWINGS

FIG. 1 is a section through a consistometer showing a portion of the cover and the vessel; and FIG. 2 is a section through the cover for the vessel of FIG. 1.

DESCRIPTION OF THE PREFERRED EMBODIMENTS

Figure 1:
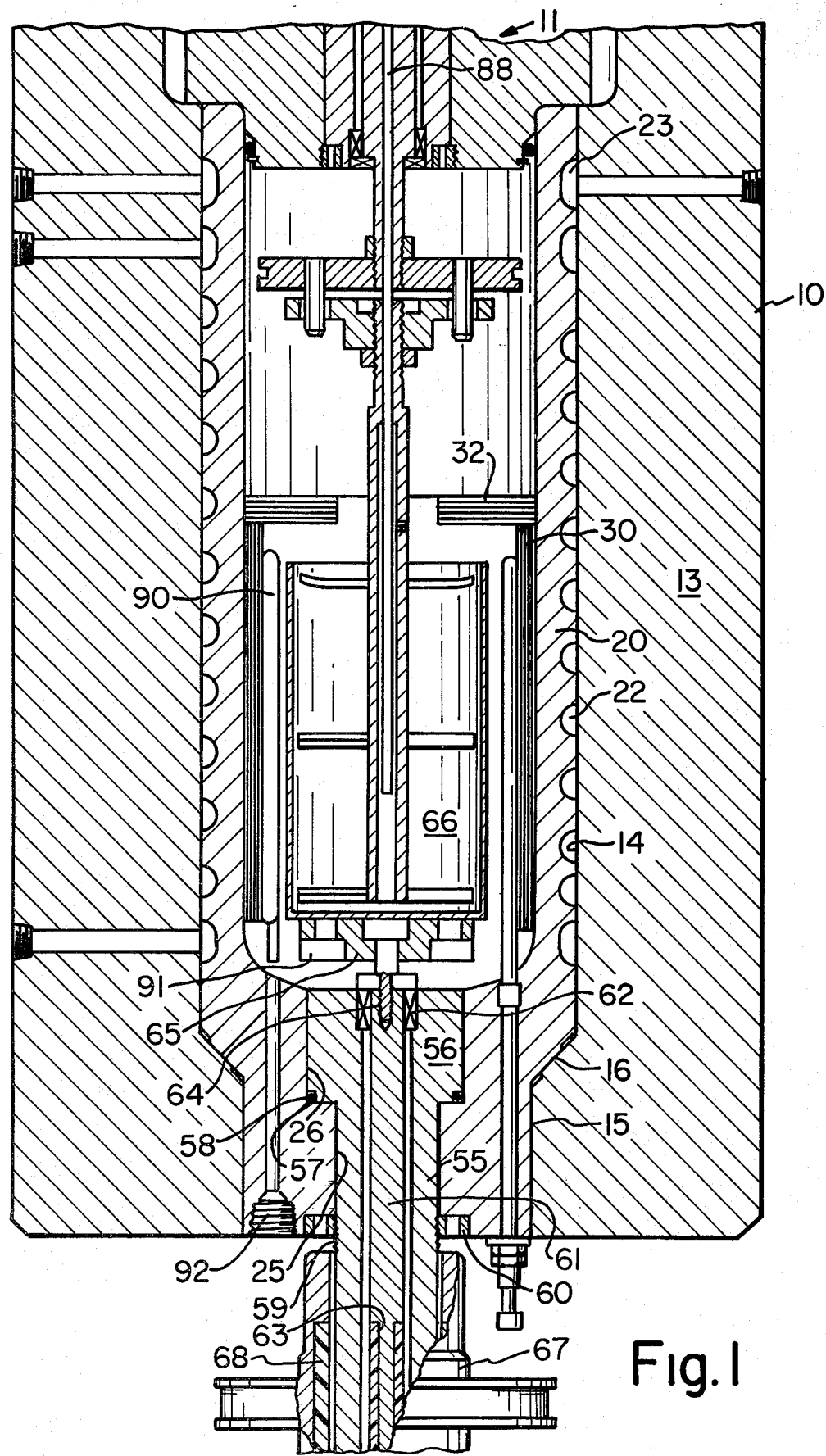
Figure 2:
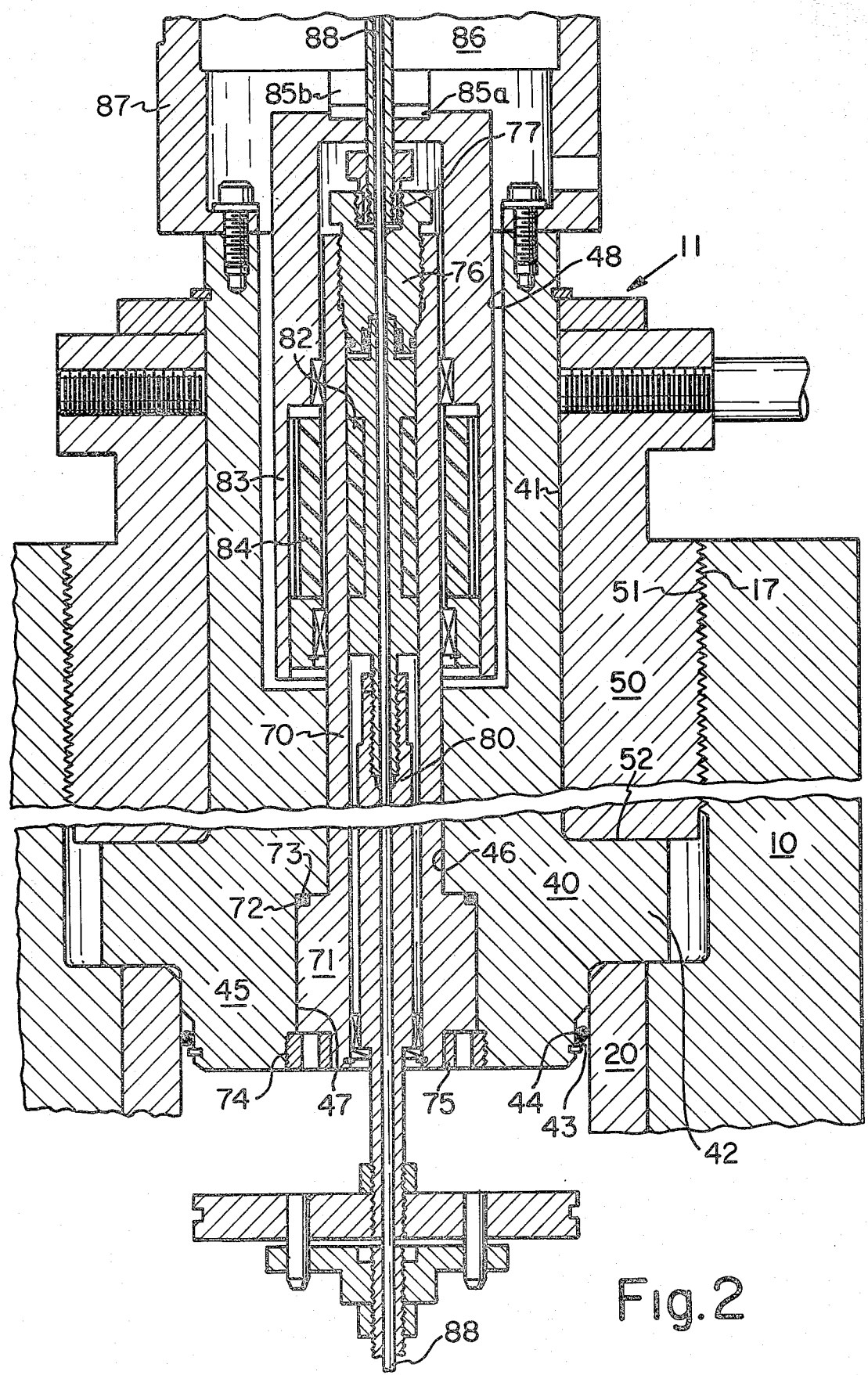

Referring now to the drawings, the consistometer comprises a water-cooled pressure vessel 10 that is generally defined by a circular cylindrical side wall, a lower end wall, and a cover. The side wall comprises an outer pressure wall 13 of suitable thickness and strength to confine the pressures of interest, say 40,000 psi. The pressure wall 13 has an inner circular cylindrical surface 14 that has a reduced inner diameter 15 at the lower end for defining a seat. The transition to the reduced diameter may be a conical surface 16. The inner surface of the pressure wall at the upper end defines large threads 17 for securing the cover. Radially inward of the inner surface of the pressure wall is a liner 20. The liner abuts the inner surface 14, the conical surface 16 and the reduced diameter surface 15 on its outer face. The conical surface or seat 16 restricts the downward axial movement of the liner 20. The liner has a groove or plurality of interconnecting grooves 22 that face the inner surface 14 of the pressure wall. These grooves are provided for the circulation of cooling liquid. Liner cooling fluid is used for cooling the vessel after the schedule is complete. In the embodiment shown in the drawing, a separate groove 23 is provided near the upper end of the liner 20. This groove is positioned to provide individual cooling for an O-ring seal to be described. The lower end of the liner 20 has a bore 25 passing therethrough with the countersunk well 26 extending from the vessel interior. A number of small bores parallel to the cylindrical axis of the vessel pass through the bottom of the liner to the interior of the vessel for permitting the passage of thermocouple leads, electrical heating element leads, and for introduction of pressurizing fluid.

Directly within the inner surface of the liner is positioned a heat shield 30. The "heat shield" protects against all three modes of heat transfer, radiation convection and conduction. The shield comprises a plurality of spaced metal or ceramic sheets. Each sheet has a different diameter and the sheets along the side wall are telescoped one over the other. The sheets are spaced apart in such a manner that the spaces therebetween are in open communication with the interior of the vessel. In other words, the pressurization of the vessel will not collapse the shield. At the top of the work chamber in the vessel, is another similar heat shield 32 having an annular configuration permitting the passage of certain shafts and thermocouple leads to be described. The top shield 32 is, likewise, a plurality of metal or ceramic sheets spaced one from the other. The particular metal for the sheets is not significant except that it should be shiny and not easily corroded. Stainless steel is an excellent choice for the heat shield.

The cover 11 comprises a central plug 40 having a circular cylindrical outer surface 41 and a collar 42 of large diameter. Near the top of the liner 20 there is a smooth circular cylindrical surface against which an O-ring seal may make a sealing contact. The plug 40 has at its lower end a seat 43 for an O-ring seal 44 on a cylindrical extension 45 beyond the collar for being inserted in the inner diameter of the liner 20 of the vessel wall to place the O-ring against the said smooth cylindrical surface.

A gland sleeve 50 has a hollow cylindrical configuration with larger external threads 51 for engaging the large internal threads 17 in the pressure vessel wall. The lower radial face 52 of the gland sleeve bears upon the collar 42 of the plug to carry the plug and to secure it in the end of the vessel. The plug 40 does not rotate with the gland sleeve and thus galling or scoring of the sealing area is avoided. Moreover, utilities passing through the plug are not subject to being twisted when the cover is placed or removed.

A permanent magnet drive is positioned at each axial end of the vessel. The drive at the bottom transfers continuous rotating motion to a shaft within the vessel. The drive at the top transfers the angular position within one revolution of a shaft within the vessel to the exterior. At the lower end a nonmagnetic canister 55 having a collar 56 of enlarged diameter seats in the countersunk well 26 and extends below the bottom of the vessel and has a sealed lower end. An annular groove 57 in the collar 56 holds an O-ring seal 58. The canister has an external thread 59 near where it emerges from the bottom of the vessel. A locknut 60 turns on the threads to secure the canister in the bottom of the liner. The seal between the liner and the canister is due to the preloading by locknut 60 of the O-ring, however. Journaled within the canister is a shaft 61 held in place by bushing 62. Keyed to the shaft are permanent magnets, preferably rare earth cobalt magnets 63, having a plurality of circumferentially spaced north and south poles. A threaded bore 64 at the end of the shaft 61 entering the vessel enables a slurry cup table 65 to be fastened thereto. A slurry cup 66 sets upon the table and is turned as the table is turned by the shaft 61. Journaled to the exterior of the nonmagnetic canister 55 is a sleeve 67 carrying permanent drive assembly. The sleeve 67 carries permanent magnet 68, preferably rare earth cobalt magnets, that are magnetized to have a plurality of circumferentially spaced north and south poles. Of course, the number of poles on the magnet within the sleeve are identical to the number of poles associated with the driven magnet keyed to the shaft 61. The sleeve 67 may be belt driven. As the sleeve 67 is turned, the shaft 61 rotates synchronously therewith.

The plug 40 has an axial bore 46 extending the entire axial length therethrough and an interior countersunk well 47 extending from the vessel interior and an exterior countersunk well 48. The cover plug 40 has a nonmagnetic canister 70 positioned in the axial bore 46. The canister has a collar 71 of increased diameter at its lower end which seats in the well 47. An annular groove 72 in the collar facing a surface of the well is arranged to receive an O-ring 73 to enable self-sealing of the canister 70 to the plug 40. The lower end of the well 47 carries internal threads 74 for receiving a locknut 75 which secures the canister to the plug. The canister 70 extends upwardly into the outer well 48 terminating near the top of the plug 40. The canister has a threaded cover 76 sealing its upper end. A sealed thermocouple feed-through 77 passes through the cover 76. An upper hollow shaft 80 is journaled in the canister by bushings and a thrust race at the lower end. The shaft extends downwardly into the vessel. The upper shaft 80 has keyed thereto permanent driving magnets 82 similar or identical to those in the lower shaft 61. A sleeve 83 is rotatably mounted to the external surface of the nonmagnetic canister 70 to be positioned substantially within the upper well 48. The sleeve carries driven magnets 84 being permanent magnets similar or identical to those in the lower sleeve 67. On top of the upper sleeve is a key 85a for receiving a keyway 85b attached to potentiometer 86 enabling transfer of torque from the sleeve to the potentiometer 86 which is fixed relative to the plug 40 by a standoff platform 87 bolted to the plug. A thermocouple 88 passes through the feedthrough in the cover 76 of the nonmagnetic canister and through the hollow shaft reaching into the interior of the slurry cup 66. The upper shaft has a plurality of paddles extending therefrom where it is within the slurry cap 66.

Heating elements 90 pass through sealed feedthroughs in the bottom of the liner. The elements are designed for alternating current power and have, for example, a 5000 watt rating. The heating elements are inside the heat shield 30. The heating elements may be controlled by a triac controller to enable programming of the heating rate of the vessel interior. A port 92 through the bottom of the lower liner enables the communication with the high pressure hydraulic system, say capable of pressurizing the vessel to 40,000 psi. The slurry cup 66 may have diaphragm cover (not shown) over the top that reduces the intermixing of the pressurized hydraulic oil with the slurry being tested. At least one thermocouple passes up through the bottom of the vessel via a sealed feed-through. This thermocouple senses the temperature of the oil within the vessel and can be used for feedback control of the heating elements.

A preferred feature according to this invention is a paddle 91 secured to the bottom of the slurry cup or to the lower shaft for promoting circulation of the oil and thus temperature uniformity in the vessel. Circulation also assists in the cool down of the vessel interior.

Having thus described the invention with the detail and particularity required by the Patent Laws, what is desired protected by Letters Patent is set forth in the following claims.

We claim:

1. A high temperature and high pressure consistometer comprising:
   a cylindrical pressure vessel having an integral bottom;
   a cover for said pressure vessel;
   means for securing and sealing the cover to the vessel;
   a nonmagnetic canister extending downwardly from said bottom and being sealed therein, a lower driven permanent magnet assembly being journaled in said canister for unlimited rotation, a drive shaft connected to said lower driven permanent magnet assembly extending into said vessel;
   a nonmagnetic canister extending upwardly from the cover and being sealed therein, an upper driving permanent magnet assembly being journaled in said canister, a shaft connected to said upper driving permanent magnet assembly extending downwardly into said vessel;
   a lower driving permanent magnet assembly mounted for rotation on the exterior of the downwardly extending canister and an upper driven permanent magnet assembly mounted for rotation on the exterior of the upwardly extending canister;
   a sample cup connected to the upwardly extending drive shaft and a paddle connected to the downwardly extending shaft being positioned within the cup;
   means for introducing pressurizing fluid into the vessel and means for heating the vessel interior;
   means external the vessel for measuring the torque magnetically transferred from the shaft carrying the paddle to the driven magnet assembly; and
   means for causing the driving magnet assembly to rotate at a constant speed to thereby drive the cup within the vessel at a constant speed.

2. A consistometer according to claim 1 further comprising a heat shield consisting of a plurality of reflective sheets surrounding the inner side wall of the vessel, the spaces between sheets being in communication with the the vessel interior.

3. A consistometer according to claim 1 further comprising a heat shield consisting of a plurality of spaced reflective sheets beneath the vessel cover, the spaces between the sheets being in communication with the vessel interior.

4. A consistometer according to claim 1 further comprising a heat shield consisting of a first group of reflective sheets surrounding the inner side wall of the vessel and a second group of spaced reflective sheets beneath the vessel cover, the spaces between said sheets in open communication with the interior of the vessel.

5. A consistometer according to claim 1 in which the vessel comprises a pressure wall having a cylindrical inner surface and a cylindrical liner having a generally cylindrical outer surface for abutting the inner surface of the pressure wall, said liner having a plurality of grooves therein defining a pathway for circulating cooling fluid, openings in the pressure wall communicating with the grooves in said liner.

6. A consistometer according to claim 1 having a paddle attached to the upwardly extending drive shaft for causing circulation of the pressurized fluid in the vessel while turning the sample cup.

7. A consistometer according to claim 5 wherein the pressure wall is thicker near the bottom of the vessel forming a seat for restricting downward movement of the vessel liner relative thereto, the liner having a countersunk well at the lower end thereof, the downwardly extending nonmagnetic canister having a collar at the upper end thereof for seating in and abutting the countersunk well.

8. A consistometer according to claim 7 wherein there is an annular groove between the surface of the well in the liner and the collar on the nonmagnetic canister for capturing an O-ring seal.

9. The consistometer according to claim 1 wherein the cover comprises a nonrotating plug having a collar at the lower end thereof, said means for securing the cover to the vessel comprising a gland sleeve slidably positioned on the plug, said gland sleeve having an axial end face for abutting the collar on the plug, said gland sleeve having external threads for engaging internal threads in the vessel, said plug having an axial bore with a countersunk well at the lower end thereof, said upwardly extending nonmagnetic canister having a collar at the lower end thereof for seating in and abutting the countersunk well.

10. A consistometer according to claim 9 wherein there is an annular groove between the surface of the well in the plug and the collar on the nonmagnetic canister for capturing an O-ring seal.

11. A consistometer according to claim 5 or 9 wherein the cover carries an O-ring seal that abuts a smooth inner cylindrical surface of the liner.

* * * * *